United States Patent [19]
Furnish et al.

[11] Patent Number: 5,797,956
[45] Date of Patent: *Aug. 25, 1998

[54] SURGICAL INSTRUMENT HANDLE AND ACTUATOR MEANS FOR HEART SURGERY

[75] Inventors: Gregory R. Furnish; W. Michael Hipps, both of Lawrenceville, Ga.

[73] Assignee: Snowden-Pencer, Inc., Tucker, Ga.

[ * ] Notice: The term of this patent shall not extend beyond the expiration date of Pat. No. 5,470,328.

[21] Appl. No.: 618,448

[22] Filed: Mar. 20, 1996

Related U.S. Application Data

[63] Continuation-in-part of Ser. No. 540,472, Oct. 10, 1995, abandoned.

[51] Int. Cl.⁶ .............................. A61B 17/28; A61B 17/32
[52] U.S. Cl. ................................. 606/205; 606/174
[58] Field of Search ......................... 606/1, 205–209, 606/169, 174, 190–198

[56] References Cited

U.S. PATENT DOCUMENTS

| | | | |
|---|---|---|---|
| 2,898,916 | 8/1959 | Kammer | 606/139 |
| 4,248,233 | 2/1981 | von Zeppelin et al. | 606/207 |
| 4,590,936 | 5/1986 | Straub et al. | |
| 4,598,711 | 7/1986 | Deniega | 606/143 |

(List continued on next page.)

FOREIGN PATENT DOCUMENTS

WO81/03122  12/1981  WIPO.

OTHER PUBLICATIONS

Promotional Literature (catalog) Medicon instrumente Microo Forceps, (date unknown).
Photocopy of actual Ethicon (MIC 608) instrument handle (date unknown).
Promotional Literature, "Diamond Line" Snowden–Pencer (1990).
Excerp from article on Laproscopic Suturing System, Karl Storz, Endoscopy–American, Inc. (date unknown).
Promotional Literature, Jarit, Inc. Mar. (1992).
Promotional Literature, Aslan Medical Technologies (date unknown).
Promotional Literature, Karl Storz Gmbh & Co. Szabo–Berci Needle Drivers (1991).
Promotional Literature, B. Braun–Dexon Gmbh (date unknown).
Promotional Literature, Access Surgical International, Inc. (Sep. 1992).
Promotional Literature, Endotec Endoscopic Technologies, Inc. (1993).
Promotional Literature, AESCULAP® ProMis Line® Pen–handle–Psalmon endoscopic–handle (Sep. 1994).

*Primary Examiner*—Glenn K. Dawson
*Attorney, Agent, or Firm*—Needle & Rosenberg, P.C.

[57] ABSTRACT

A hand-held surgical instrument with an improved handle, the instrument being of the type generally comprised of a handle and a tool with a body member having at least one articulated member thereon, is provided. The handle has an elongated base, an elongated lever with a downwardly projecting actuator arm and structure for connecting the lever and base at a rearward pivot point, which mimics the natural pivot point of the surgeon's hand. The surgical tool may be activated by moving an actuator rod distally by closing the handle lever. The lever may be biased by a spring longitudinally positioned around the actuator rod within the base, in an open position. The instrument includes structure for securing the handle at selected points throughout a range of motion or, alternatively, allowing motion that is not locked at any position. Also provided is a collar for allowing rotation of the tool to a desired radial orientation and adjustably securing the tool in that orientation.

6 Claims, 10 Drawing Sheets

U.S. PATENT DOCUMENTS

| | | |
|---|---|---|
| 4,644,651 | 2/1987 | Jacobsen . |
| 4,777,948 | 10/1988 | Wright ................................. 606/171 |
| 4,950,273 | 8/1990 | Briggs ................................. 606/113 |
| 4,957,500 | 9/1990 | Liang et al. ........................ 606/205 |
| 5,009,661 | 4/1991 | Michelson ......................... 606/205 |
| 5,195,505 | 3/1993 | Josefsen . |
| 5,199,419 | 4/1993 | Remiszewski et al. . |
| 5,250,073 | 10/1993 | Cottone, Jr. ....................... 606/206 |
| 5,273,519 | 12/1993 | Koros et al. ....................... 606/171 |
| 5,304,203 | 4/1994 | El-Mallawany et al. ........... 606/205 |
| 5,330,502 | 7/1994 | Hassler et al. .................... 606/205 |
| 5,336,238 | 8/1994 | Holmes .............................. 606/205 |
| 5,342,391 | 8/1994 | Foshee et al. ..................... 606/205 |
| 5,466,243 | 11/1995 | Schmieding et al. .............. 606/232 |
| 5,470,328 | 11/1995 | Furnish et al. .................... 606/205 |
| 5,498,256 | 3/1996 | Furnish ................................. 606/1 |
| 5,624,431 | 4/1997 | Gerry et al. .......................... 606/1 |

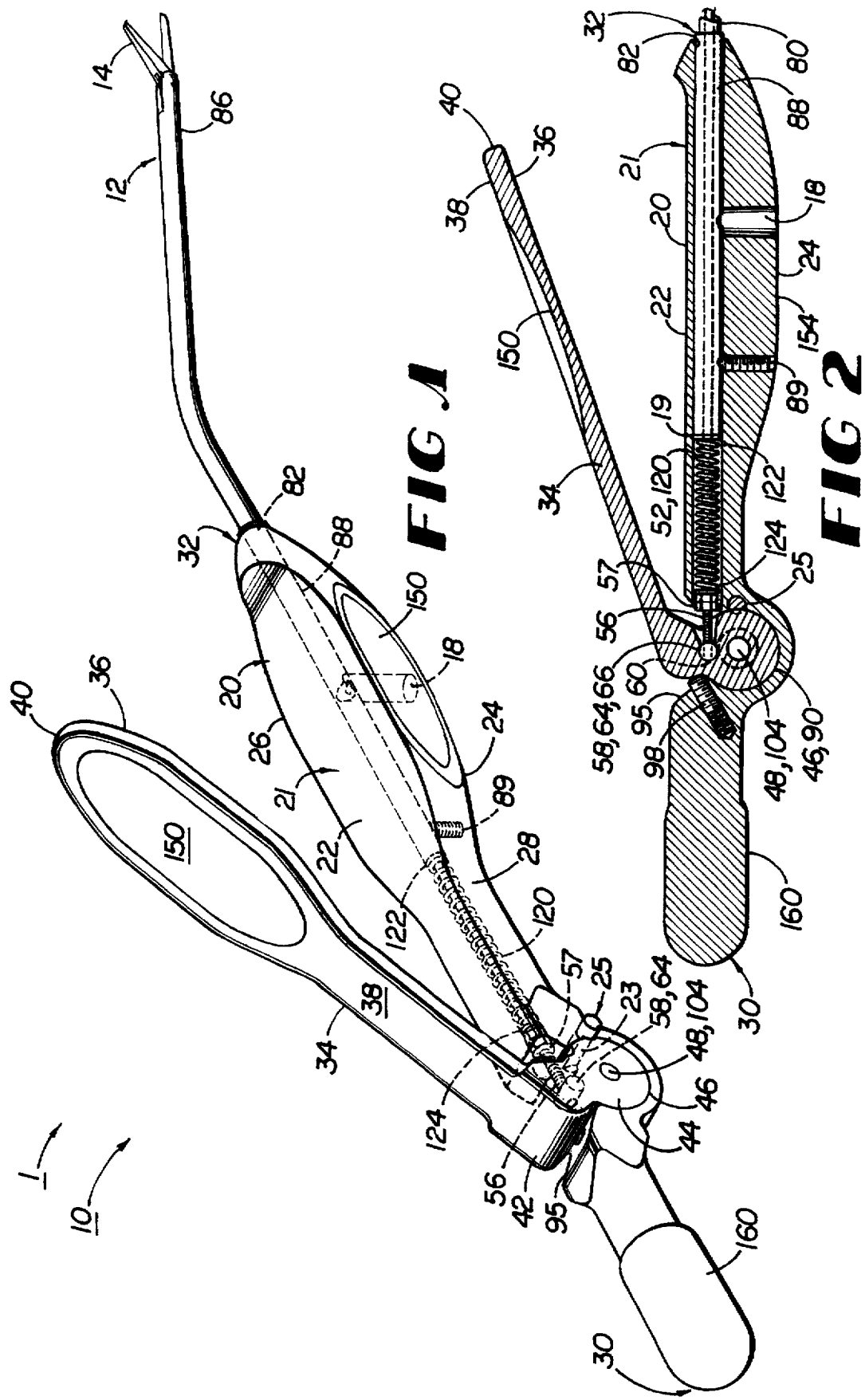

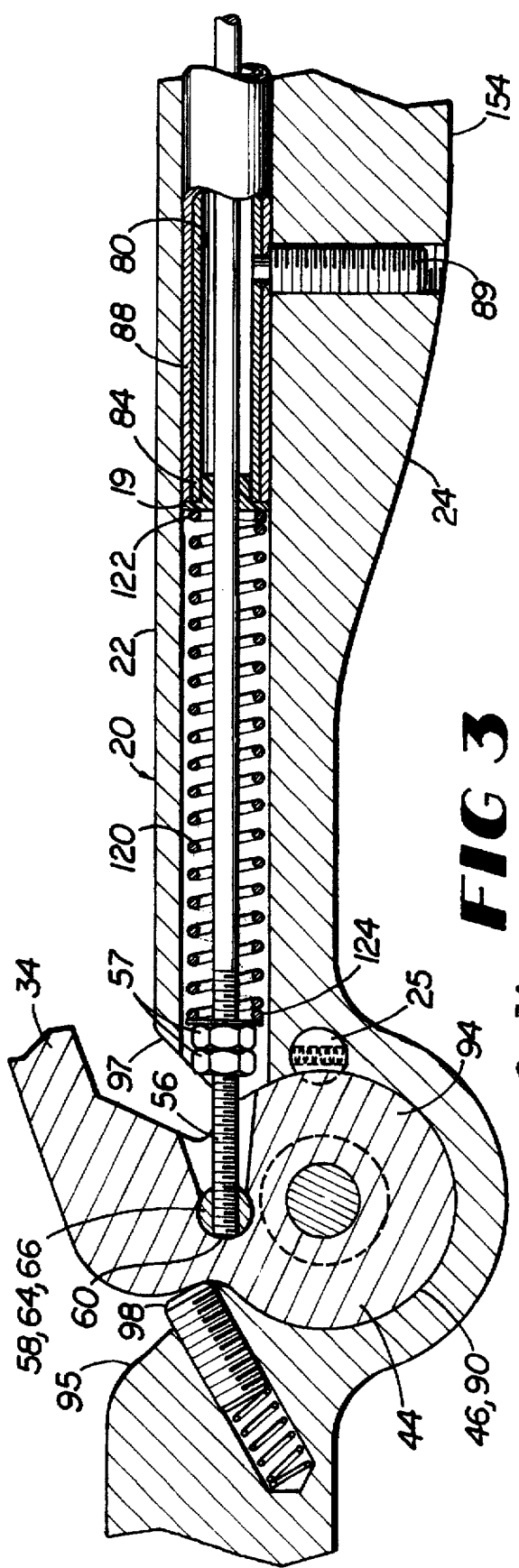
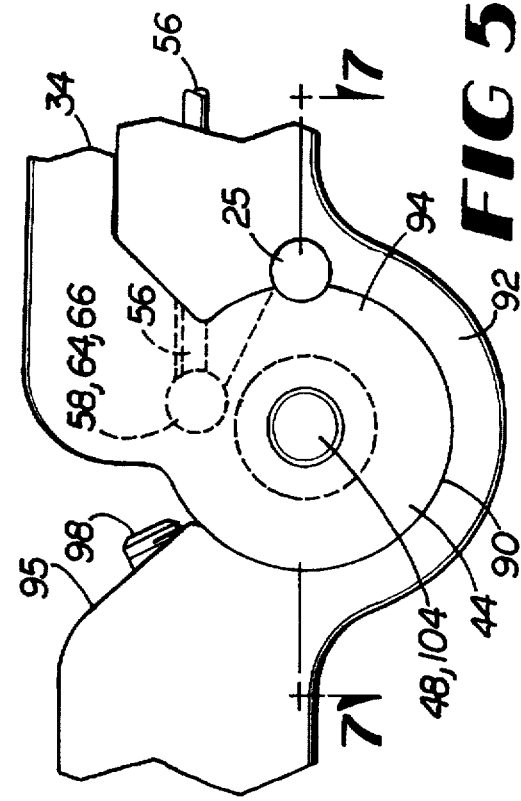
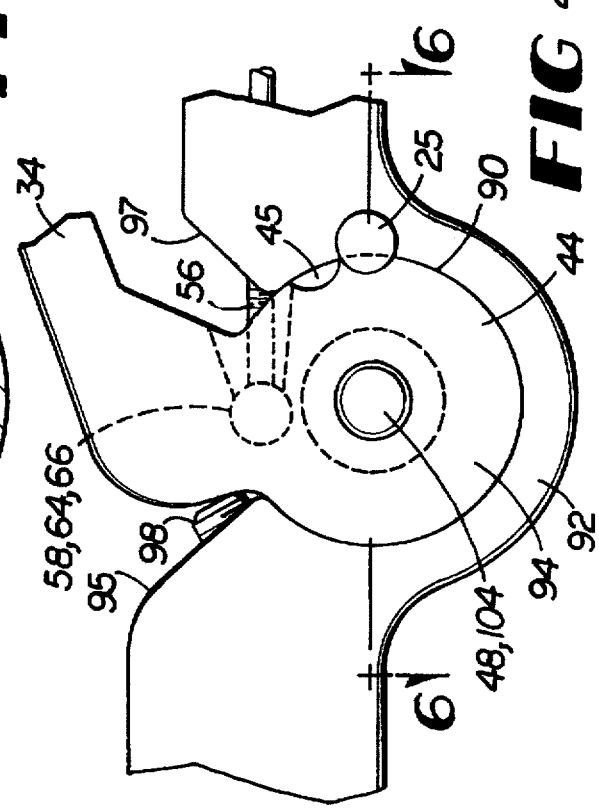

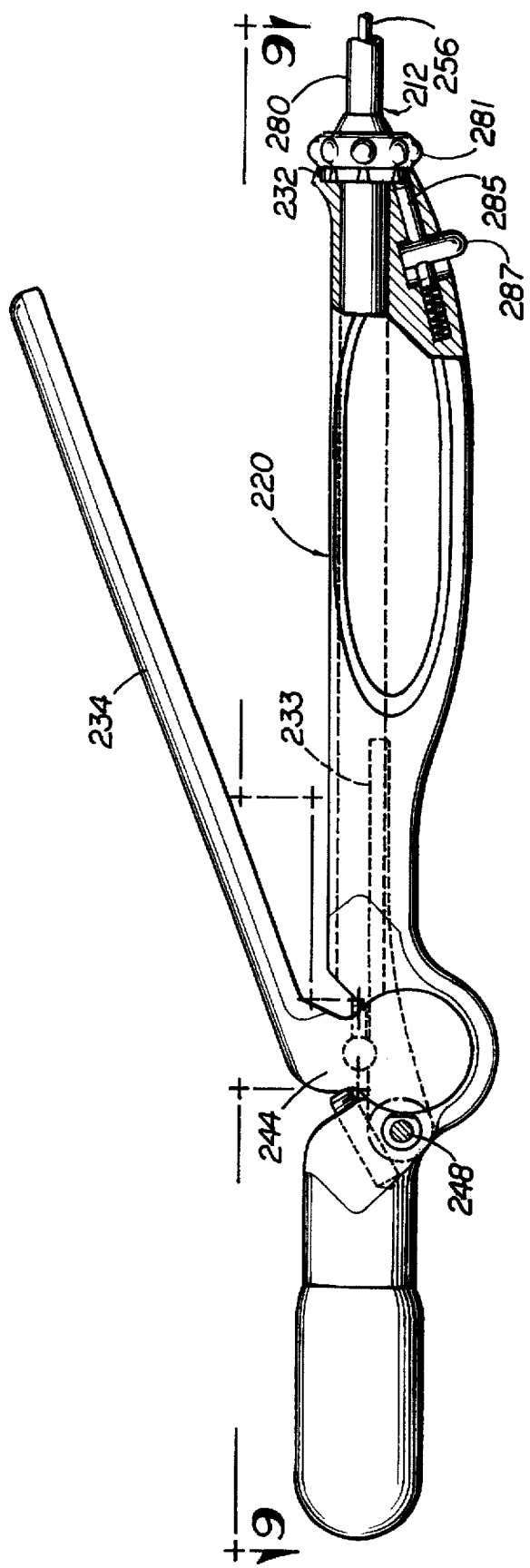
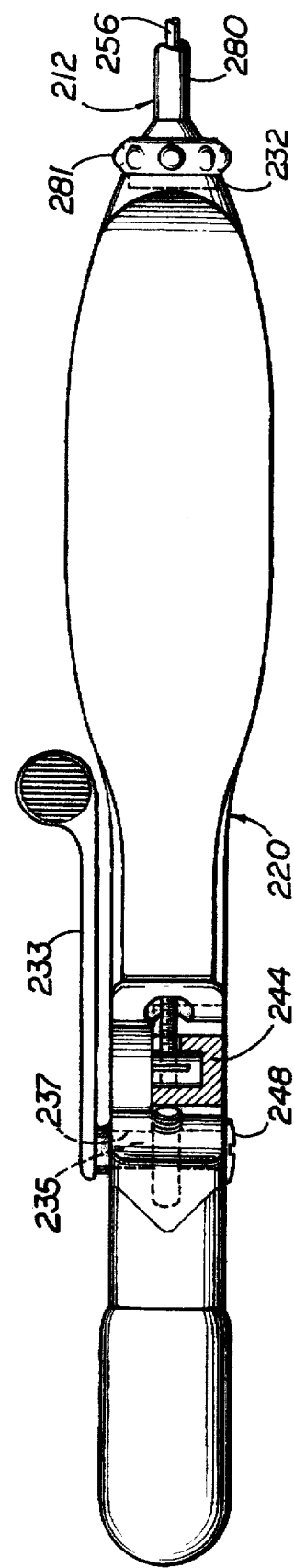
FIG 8
FIG 9

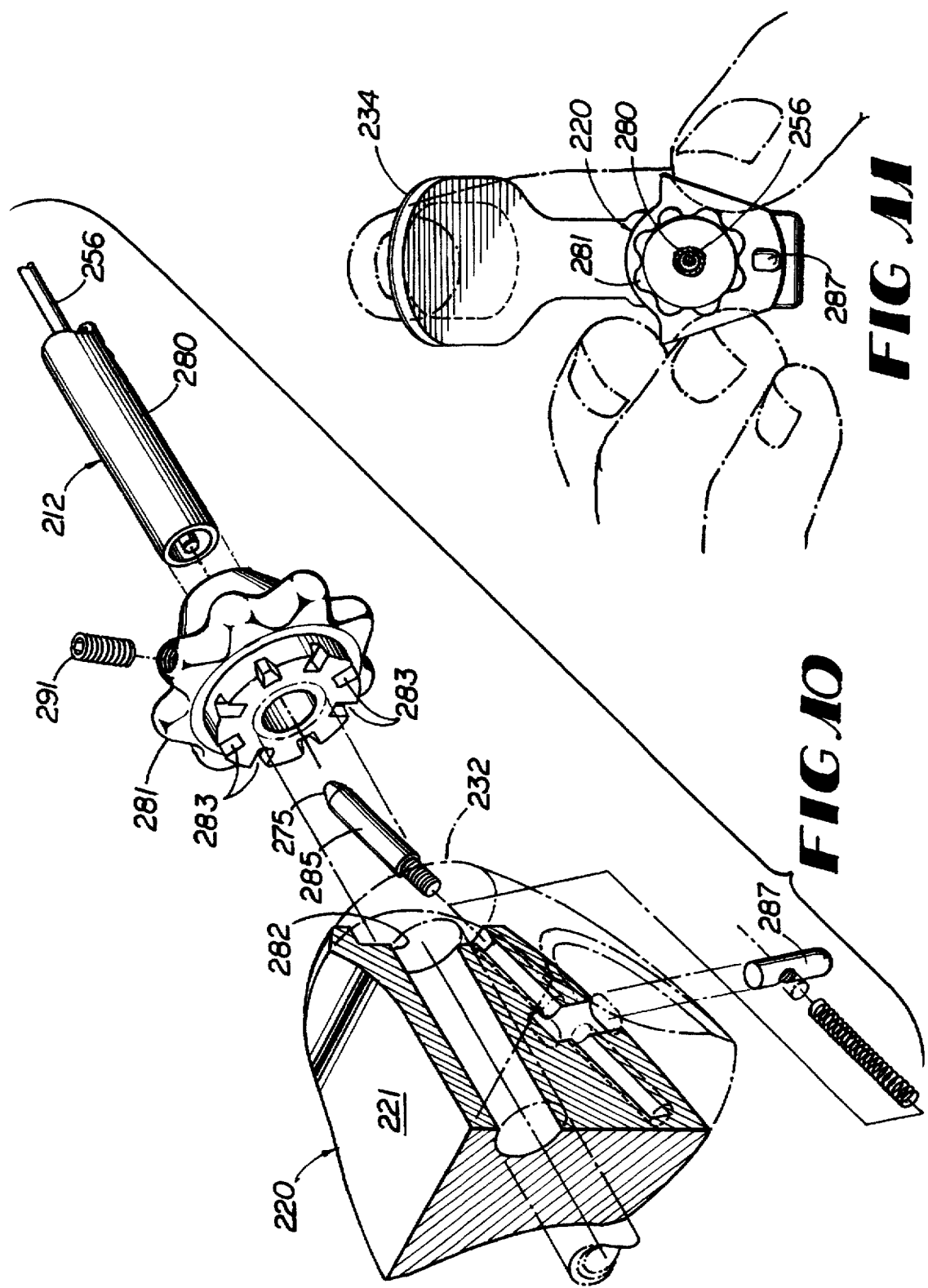

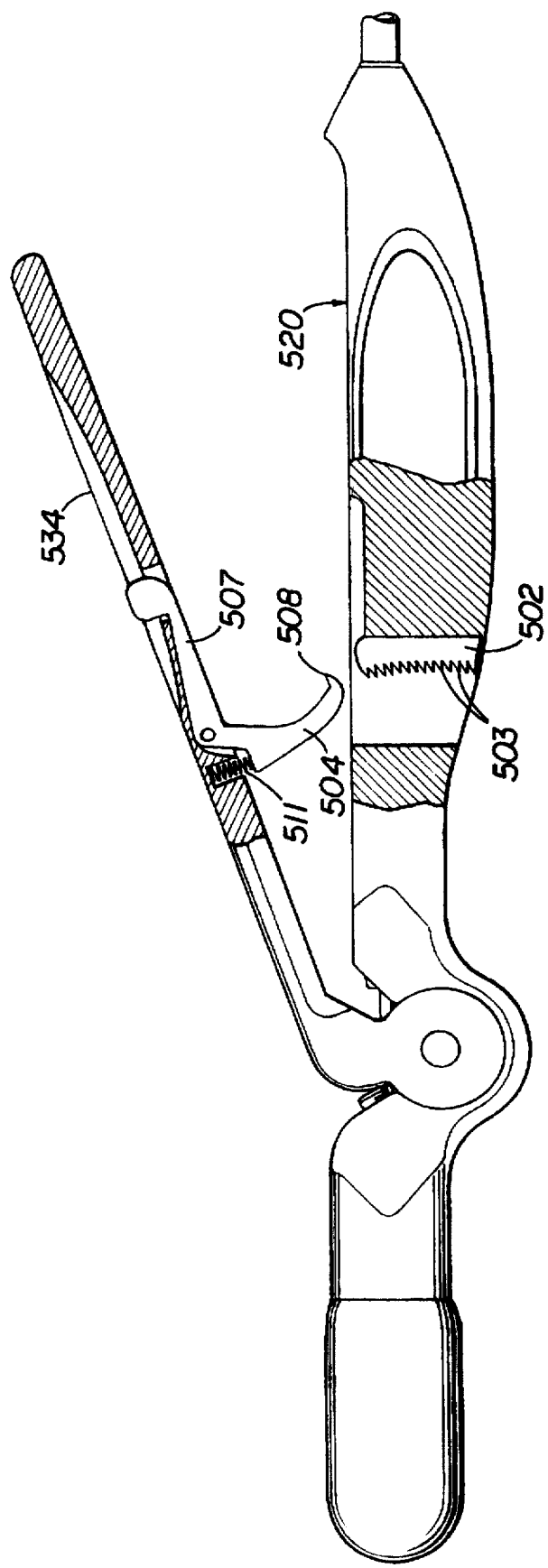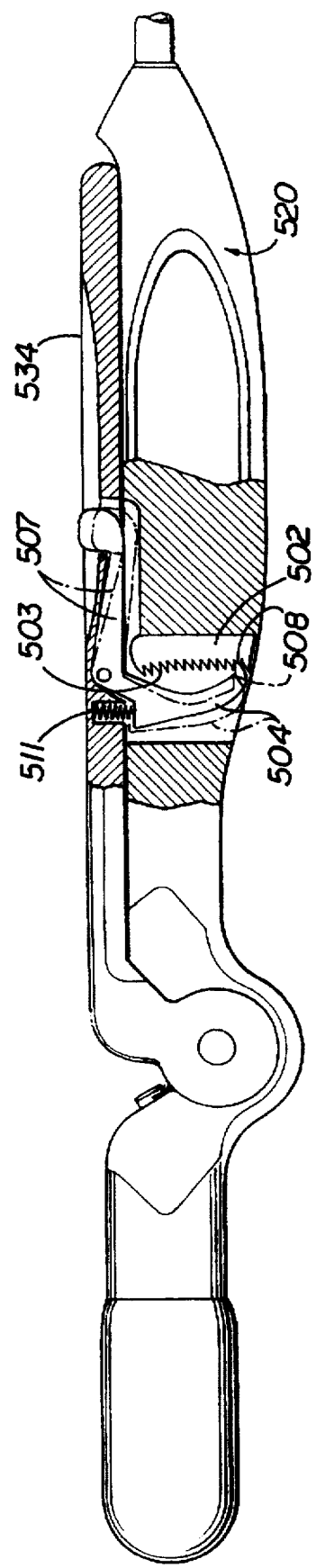

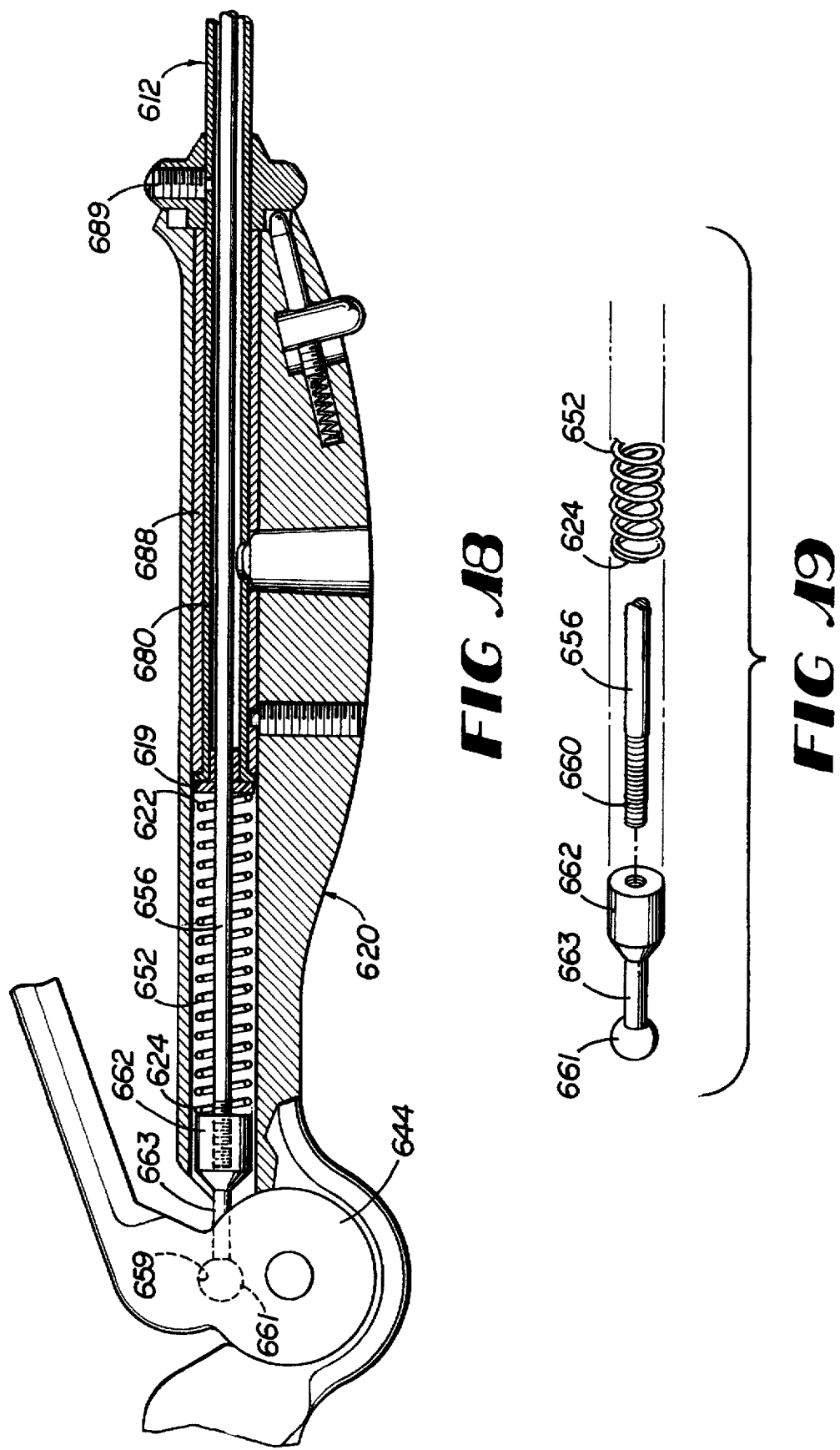

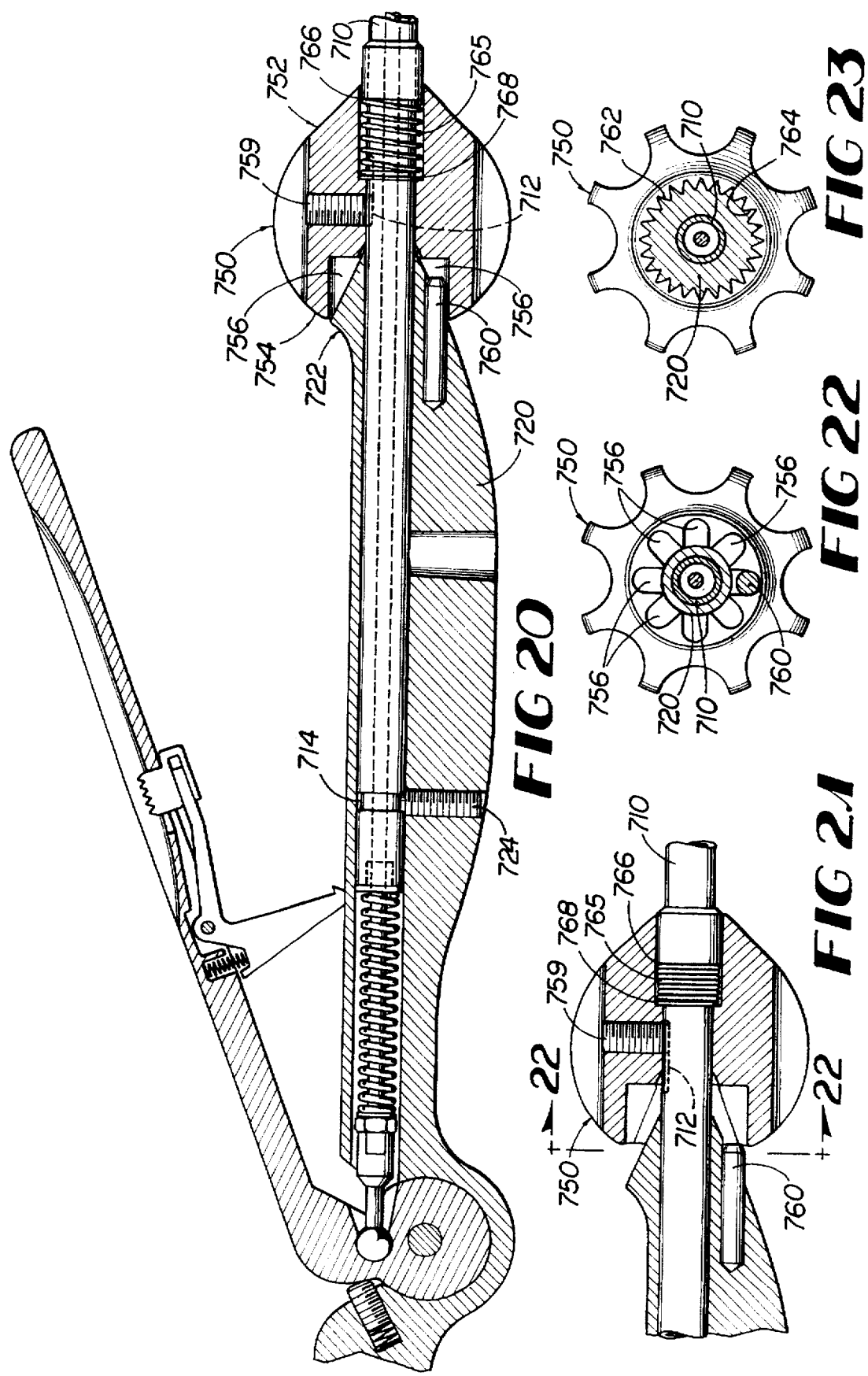

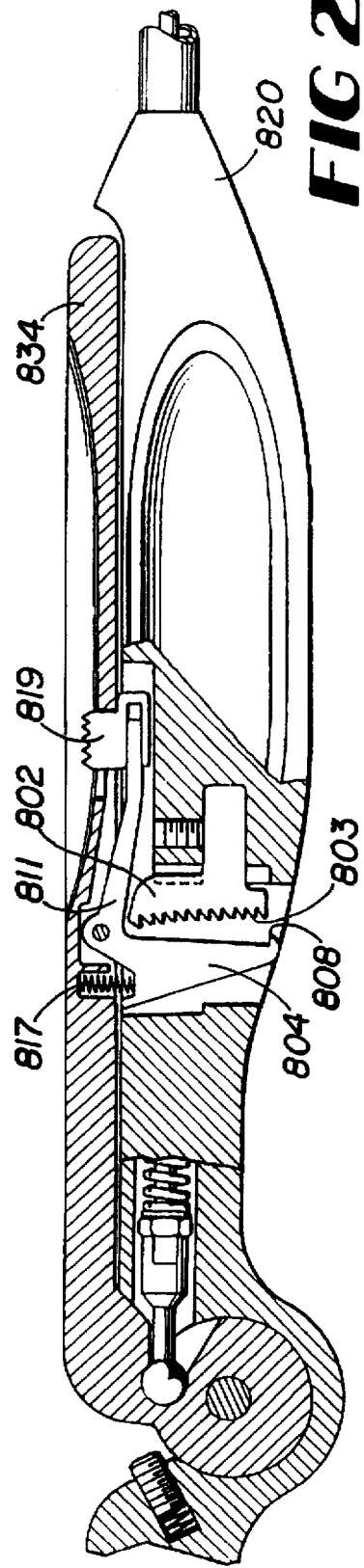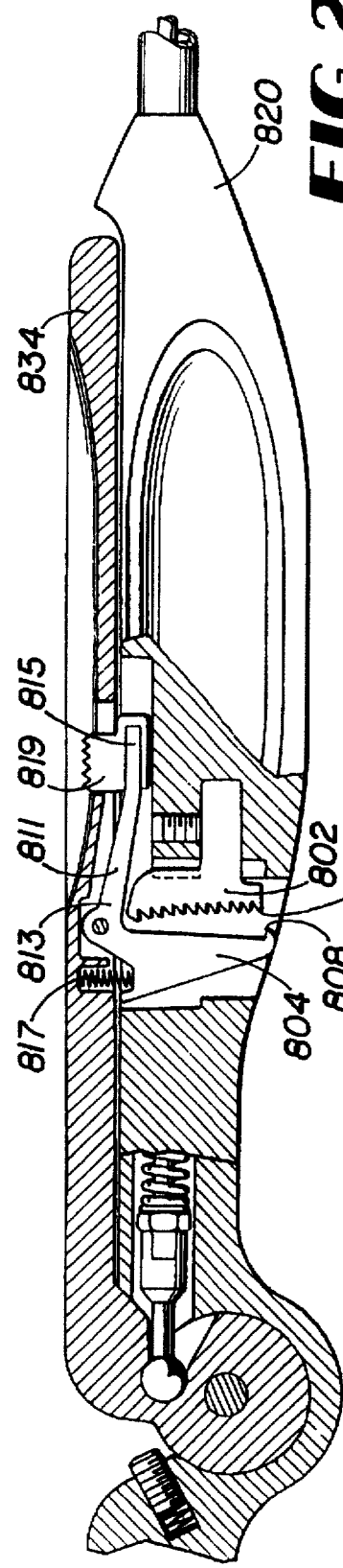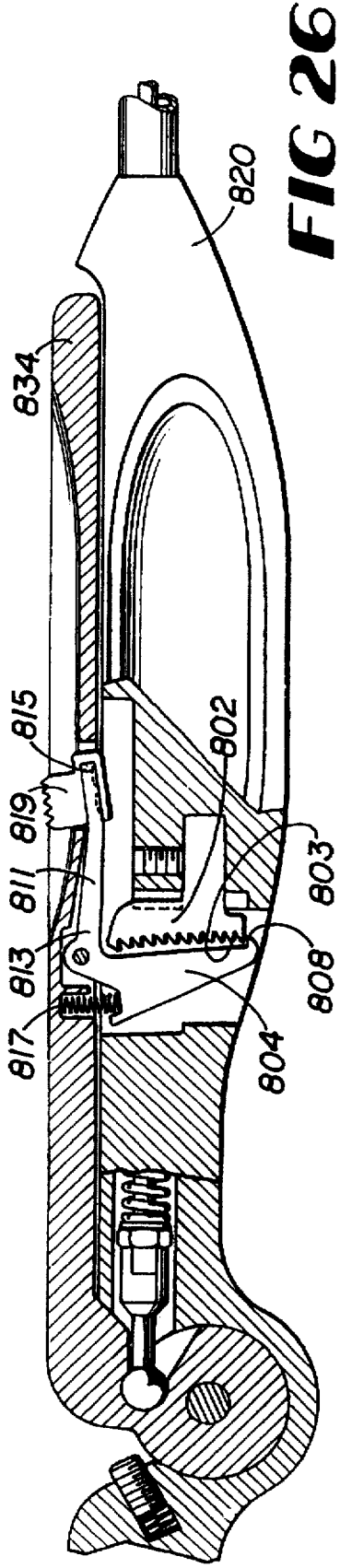

SURGICAL INSTRUMENT HANDLE AND ACTUATOR MEANS FOR HEART SURGERY

This application is a continuation-in-part of application Ser. No. 08/540,472, filed on Oct. 10, 1995, abandoned.

BACKGROUND OF THE INVENTION

1. Field of the Invention

This invention relates to handles for surgical instruments, including heart surgery instruments. In particular, this invention relates to an improved handle for hand held surgical instruments of the type having a tool with at least one articulated member thereon wherein the handle has a means for actuating the articulated member and selectively locking or disengaging from locking the articulated member intermittently in an open or closed position. This invention also encompass a handle which allows rotation of the tool to a desired radial position.

2. Background Art

Surgery is a learned art requiring many hours of advanced training and skills development that extends far beyond a thorough understanding of the medical principles involved, e.g., anatomy, physiology, principles of wound healing, and the like. The surgeon must also develop hand-to-eye coordination and acquire skills in the art of atraumatic tissue manipulation utilizing a variety of highly specialized surgical instruments.

The surgical instrument actually becomes an extension of the surgeon's hand. The surgeon must develop an ability to feel and respond, often delicately yet firmly, through his surgical instruments. Accordingly, there exists a need for instrument handles which are sensitive, responsive and ergonomically designed to augment the natural motions of the human hand.

The actuating mechanism for handles of currently available surgical instruments are usually configured such that the pivot point is located between the handle lever and the articulated member (a forwardly located pivot point). The handle can have either one or two lever arms which are moveable about the pivot point. Such configuration is opposite to the natural pivot points of the hand.

One example of prior art handles of the type described above is the conventional "scissors" type handle with a forward pivot point, e.g., Mayo or Metzenbaum scissors, or Debakey forceps. The scissors handle design usually lacks a means for biasing the instrument tool in an open position. Of necessity, therefore, these scissors type handles have finger and thumb rings located at the free ends of the lever arms which provide a means for receiving force and balancing the instrument when both opening and closing the lever arms of the handle.

The scissors type handles are usually held by inserting the thumb through the thumb ring, balancing the scissors against the index finger and inserting one or more of the remaining digits into the finger ring of the opposite lever. Movement of the lever arms is accomplished by apposing the thumb and digits which are in the finger ring. This design requires increased muscular effort to open and close the levers and, therefore, fatigues the hand of the surgeon.

A second example of the forward pivot point configuration is the "pliers" type handle which is functionally similar to the scissors handle but without finger rings. In this configuration, movement of the levers from the open to the closed position is accomplished by closing the palm of the hand in a squeezing motion. A bow spring or other spring configuration located between the lever arms is sometimes included as a means to bias the handle in an open position to compensate for the lack of finger rings.

Neither the scissors nor the pliers type of handles are capable of being held and moved by the tips of the fingers, which results in a significant loss in sensitivity.

A third type of handle utilizes an actuator having two bowed springs connecting a rearwardly projecting actuator rod to handle levers which pivot about a forward pivot point. Although this handle may be held in a manner which allows for fingertip control, the forwardly located pivot point, opposite from the natural pivot point of the hand, results in loss of leverage and decreased sensitivity of the instrument. For fingertip control, the surgeon must sacrifice leverage by placing the fingertips away from the lever ends and closer to the forward pivot point.

One type of instrument which utilizes a rearwardly located pivot point is the forcep, e.g., Adison, Potts-Smith, or general tissue forceps. Forceps utilize the thumb and index finger in a "pencil" grip fashion. However, forceps are not designed to activate an articulated member of a tool. e.g., a needle holder, retractor, or hemostat. Rather the distal ends of the forcep lever arms actually comprise the tool itself.

The present invention satisfies the need in the art for a more sensitive and ergonomic handle by providing an instrument handle that is designed to functionally mimic and create functional harmony with the natural gripping mechanism and motion that exists between the thumb and index finger of the human hand.

The invention also provides an actuating means which moves forward to manipulate the tool when the handle level is depressed into the closed position. The invention also provides a biasing means to maintain the handle in the open position. The present invention additionally provides a means for locking the handle in a variety of positions, including the open and the closed positions, or, alternatively, unlocking the locking means to provide free movement of the handle. The invention also provides a means for rotating the surgical tool so that the tool can be disposed at a desired radial orientation. The invention satisfies the need for a surgical handle that is simpler to manufacture, assemble and disassemble than the prior art.

SUMMARY OF THE INVENTION

The present invention provides a surgical instrument with an improved instrument handle with a base and lever, with an activating arm that is connected to the base at a rearwardly located pivot point. The instrument is designed to be held in a "pencil grip" or "Vardon golf grip" position; both of which are natural gripping relationships between the index finger and opposable thumb.

The rearwardly located pivot point on a downwardly projecting actuator arm of the lever of the invention provides great versatility in gripping positions. In a pencil grip type of position, the actuator can be operated either by the index finger, or turned 90 degrees for operation by the thumb. Alternatively, the instrument can be held in a golf club grip type of position for operation of the actuator with the thumb. The ergonomic design permits the surgeon to transfer force in a direct relationship from the hand to the articulated member of the surgical tool with precision, ease and delicacy.

The present invention also provides a means for actuating the articulating member of the tool by depressing the handle, which moves the actuating rod forward. In the preferred embodiment, this actuating means serves to close the articulating member, such as one side of a pair of forceps or scissors.

The invention also provides a coil spring that functions as a means for biasing the lever in an open position. This feature allows the resistance and sensitivity of the lever to be varied by changing the thickness and resistance of the spring. The coil spring is positioned longitudinally around the actuator rod within the handle base.

The invention further provides elongated ergonomically adapted finger pads on the sides of the base. The base can be further equipped with a rearward counterweight to counteract the weight of the tool on the opposite end. Furthermore, the tool may be rotatable through a variety of positions. The instrument may be equipped with a means for locking the handle in a variety of positions, including the open and closed positions.

Additionally, the pivot point (or hinged joint) of the handle of the invention is designed for easy manufacture, assembly and disassembly. A single fixation means forms a transverse pivot point which connects the actuator arm and base. These and other features of the present invention will become apparent in light of the specification as a whole.

BRIEF DESCRIPTION OF THE DRAWINGS

FIG. 1 is a right-side rear perspective view of a first embodiment of the present invention in the open position.

FIG. 2 is a right-side elevation longitudinal cross-section view of the first embodiment showing the surgical instrument handle in the open position.

FIG. 3 is a detail portion of FIG. 2 showing the means for biasing the surgical instrument handle in the open position.

FIG. 4 is a detail right-side view of the first embodiment of the invention showing the handle in the open position with the actuator means in phantom lines.

FIG. 5 is a detail right-side view of the first embodiment of the invention showing the handle in the closed position with the actuator means in phantom lines.

FIG. 8 is a right-side elevational view of a second embodiment of the invention showing a selective lever position locking means in phantom lines and a tool orienting means.

FIG. 9 is an overhead view of the second embodiment of the invention with a partial sectional view taken along lines 9—9 of FIG. 8 showing a selective lever position locking means.

FIG 10 is right-side exploded detail perspective view of the second embodiment of the present invention showing the tool orienting means.

FIG. 11 is a front end view of the second embodiment of the invention showing the tool orienting means.

FIG. 16 is a right-side partial sectional view of a fifth embodiment of the present invention showing the rachet and pawl of an alternate selective lever position locking means in the unlocked position.

FIG. 17 is a right-side partial sectional view of the fifth embodiment of the present invention showing the rachet and pawl of an alternate selective lever position locking means in the locked position.

FIG. 18 is a detail right-side longitudinal section view of a sixth embodiment of the present invention showing an alternate actuator rod and biasing means configuration.

FIG. 19 is a detail right-side view showing the alternate actuator rod and adapter of the sixth embodiment of the present invention.

FIG. 20 is a right-side partial sectional view of a seventh embodiment of the present invention showing the tool positioning means for orienting the tool to a desired radial orientation.

FIG. 21 is a detail of FIG. 20 showing the rotatable tool orienting collar of the tool positioning means in the extended position.

FIG. 22 is a cross-sectional view of FIG. 21 taken along line 22—22.

FIG. 23 is a view of an alternative embodiment of FIG. 22.

FIG. 24 is a right-side partial sectional view of a eighth embodiment of the present invention showing the means for securing the handle at selected points throughout the range of motion, the securing means being disengaged.

FIG. 25 is a view of FIG. 24 in which the securing means is engaged and in the unlocked position.

FIG. 26 is a view of FIG. 24 in which the securing means is engaged and in the locked position.

DETAILED DESCRIPTION OF THE INVENTION

Figure 6:
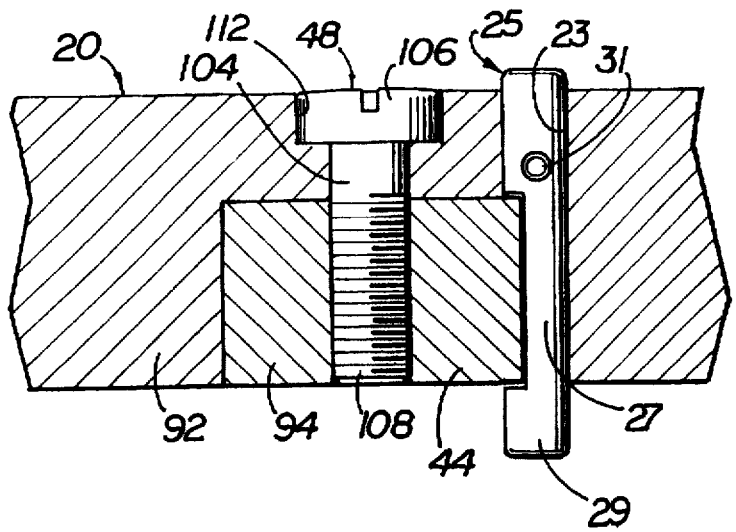
FIG. 6 is a detail cross-section view of the present invention taken along lines 6—6 of FIG. 4 showing the lever position locking means of the first embodiment.

The present invention may be understood more readily by reference to the following detailed description of specific embodiments and the Figures included herein. As used in herein, "a" may mean one or more than one, depending upon the context within which it is used.

Referring now to FIGS. 1–5, the present invention provides a hand-held surgical instrument comprising an improved handle 10 attached to a tool 12 having at least one articulated member 14 thereon. The tool 12 may be any one of a variety of a conventional surgical tools which has articulating, or moving, parts, such as scissors, hemostats, forceps, suture holders, biopsy retrievers, retractors, staplers and the like. The handle 10 has an elongated base 20 having a body portion 21, a top surface 22, opposite bottom surface 24, a first side 26 and an opposite second side 28, a proximal end 30 and a distal end 32. The handle 10 also has an elongated lever 34 having a first surface 36, an opposite second surface 38, a front end 40, a rear end 42 and an actuator arm 44 adjacent the rear end 42. The actuator arm 44 is adapted to be projected into the body portion 21 of said base 20 at a predetermined point 46. The predetermined point 46 may vary in position relative to the body portion 21 and the lever 34, depending upon the specific requirements of the surgeon and the tasks to be performed with the tool 12.

The handle 10 also has a means 48 for connecting said actuator arm 44 to said base 20 at the predetermined point 46 to allow said lever 34 to pivot about a linear transverse axis 50 at the predetermined point 46 between a normally open position (shown in FIG. 4) and a closed position (shown in FIG. 5). The base 20 and the lever 34 are juxtaposed to each other along their length, defining a longitudinal axis. The lever 34 extends forward along the longitudinal axis from said connecting means 48 toward the distal end 32 of said base 20, such that the first surface 36 of said lever 34 is adjacent to the top surface 22 of said body portion 21.

The handle 10 also has a means for biasing said lever 34 in the normally open position. Additionally, the handle 10 is provided with a means for actuating the articulated member 14 of the tool 12, wherein an actuator rod 56 is pivotally connected at a fixed point 58 on the actuator arm 44 of said lever 34, such that moving said lever 34 from the normally open position (FIG. 4) to the closed position (FIG. 5) causes said fixed point 58 on the actuator arm 44 to be displaced distally 32, thereby moving said actuator rod 56 toward the distal end 32 of the base 20, and causing movement of the articulated member 14. The fixed point 58 may be positioned in a variety of locations on the actuator arm 44 depending upon the range and force of actuating motion desired and the size and purpose of the tool 12.

In a first embodiment of the surgical instrument, shown particularly in FIGS. 1–5, the actuator rod 56 further comprises a first end 60 and a second end (not visible), the second end of the rod 56 being connected to the articulated member 14 of the tool 12, and the first end 60 of the rod 56 being connected to the actuator arm 44 at the fixed point 58. In this embodiment, the rod 56 is disposed through the body portion 21 of the base 20, such that movement of the lever 34 from the normally open position (FIG. 4) to the closed position (FIG. 5) causes the first end 60 of the rod 56 to be displaced toward the distal end 32 of the body portion 21 of the base 20, thereby moving the articulated member 14 of the tool 12.

In the first embodiment of the instrument, the first end 60 of the actuator rod 56 comprises a pin 64 which is inserted into a complimentary receptacle 66 at the fixed point 58 on the actuator arm 44, thereby pivotally connecting the actuator arm 44 to the actuator rod 56. The pin 64 and complimentary receptacle 66 are shown to be round in shape, however, a variety of other shapes and configurations which permit a pivotal connection are contemplated.

In the first embodiment, the tool 12 may further comprise a body member 80 wherein the base 20 defines an opening 82 at the distal end 32 thereof complementary to the shape of a first end 84 of the body member 80 of the tool 12, such that the body portion 21 of the base 20 attachably receives therein the first end 84 of the body member 80, and wherein the articulated member 14 is pivotally attached to an opposite second end 86 of the body member 80. Furthermore, the instrument can have a hollow elongated tube 88 having the body member 80 and the actuator rod 56 disposed therethrough. The slidable actuator rod 56 is of the type commonly used in the art for endoscopic instruments, which require movement of a tool. The invention also contemplates the absence of either the hollow tube 88 or body member 80 such that the actuator rod 56 may not be slidably housed within a hollow elongated tube 88 or body member 80, but rather project directly from the body 21 of the base 20 unhoused. In the sectional view of the first embodiment of the present invention shown in FIG. 3, a dog point set screw 89 serves to secure the elongated tube 88 within the base 20.

The instrument of the present invention further has a joint 90 for connecting the base 20 of the handle 10 to the actuator arm 44 of the lever 34 at the predetermined point 46. The joint 90 has a circular hinge socket 92 on the base 20 at the predetermined point 46 which is journalled for motion about the transverse axis, and a hinge barrel 94 on the actuator arm 44 dimensioned to be received within the hinge socket 92. By journalled, it is meant that the socket 92 has been configured, as by machine routing or original dye casting, to receive the hinge barrel 94. This joint 90 allows the actuator arm 44 to pivot about the transverse axis at the predetermined point when the lever is moved between the normally open position (FIG. 4) and the closed position (FIG. 5). The configuration of the base 20 at the joint 90 also provides an open-lever stop 95 and a closed lever stop 97, which define a maximum range of motion for the lever 34. The invention may be provided with an open-lever set screw 98, which is rotated to adjust the range of lever motion. Of course, a stop-lever set screw (not shown) could also be provided on the closed-lever stop 97. The joint 90 is shown as a hinged socket, however, a variety of other joints are contemplated for pivotally connecting the base 20 to the lever 34 as would be apparent to one skilled in the art.

The connecting means 48 of the first embodiment comprises a continuous bore extending along the transverse axis through the base 20 and through the actuator arm 44. The bore on the actuator arm 44 has internal threads to receive a fixation screw 104 having a head end 106 and an opposite tail end 108 having threads complimentary to the internal threads, the screw 104 passing through the bore of the base 20 such that the head end 106 of the screw 104 rests within a counterbore 112 on the first side 26 of the base 20. The connecting means 48 is shown as comprising a threaded fixation screw 104, allowing rotational movement of the actuator arm 44, however, a variety of other connecting means are contemplated by the invention, such as bolts, rivets or other fasteners. The connecting means for example, can be of the shoulder screw type that prevents clamping of the actuator arm 44 relative to the base 20. Alternate single connecting means are described more fully below with reference to the second embodiment shown in FIGS. 8–12, and the third embodiment shown in FIG. 13. The single connecting means provide the invention with a greatly increased ease of assembly and disassembly.

The invention also provides a biasing means for biasing the lever 34 in the normally open position, as shown in FIGS. 1–3. The biasing means of the first embodiment of the instrument is a compression coil spring 120 having a preselected thickness and which is longitudinally positioned around the actuator rod 56 within the base 20. The preselected thickness and coiling of the spring 120 wire is intended to vary according to the resistance and sensitivity desired by the surgeon for the particular tool 12. The compression spring 120 is maintained in compressed elongated alignment within the handle 10 of the instrument such that compression spring 120 urges the lever 34 toward the normally open position. More specifically, the compression spring wire 120 has a first end 124 and a second end 122, and the base 20 has a recess therein for receiving the second end 122 of the compression spring wire 120, such that the recess holds the compression spring in alignment with the longitudinal axis against the elongated hollow tube 88. The first end 124 of the spring wire 120 can be positioned adjacent a pair of adjustable tension nuts 57. The second end 122 of the spring wire 120 is abutted adjacent a bushing 19. Therefore, in this position, the compression spring 120 urges the lever 34 toward the normally open position.

The first and second sides 26, 28 of the base 20 and the second surface 38 of the lever 34 each are equipped with an ergonomically adapted finger pad 150. These pads 150 assist the surgeon in maintaining a comfortable and secure grip on the instrument. The ergonomically adapted finger pads 150 are adapted for holding between the operator's thumb and fingers. The first and second sides 26, 28 have opposing concave curvatures corresponding to the shape of human digits. Furthermore, the bottom of the sides 26, 28 converge toward each other at the bottom surface 24 such that the top surface 22 is wider than the bottom surface 24. The two sides 26, 28 of the base 20 can each terminate in support feet 154 which allow the instrument to stand independently.

The base 20 can further comprise a counterweight 160 positioned within the proximal end 30 of the base 20 to balance the instrument at a second predetermined point (not shown). The second predetermined point will vary depending upon the combination of the mass of the counterweight 160 and the mass of the surgical tool 12. It is contemplated that the second predetermined point could be adjusted in the surgeon's hand by rotating the counterweight 160, thereby changing the distance between the counterweight 160 and the transverse axis 50. For example, the counterweight 160 may be attached to the base 20 by means of an elongated threaded rod (not shown) on the base 20 which is received into a complimentarily threaded opening in the counterweight 160. By rotating the counterweight 160 the distance between the counterweight 160 and the transverse axis 50 changes, and thus also the second predetermined point.

Figure 7:
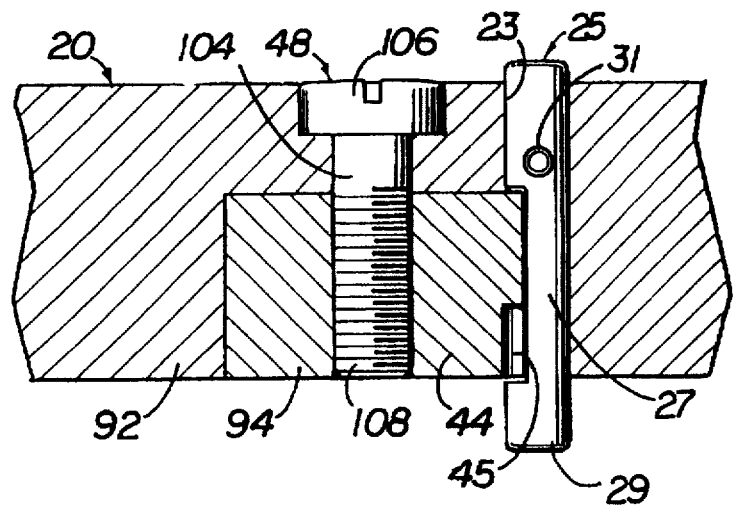
FIG. 7 is a detail cross-section view of the present invention taken along lines 7—7 of FIG. 5 showing the locking pin in the unlocked position.
Figure 7A:
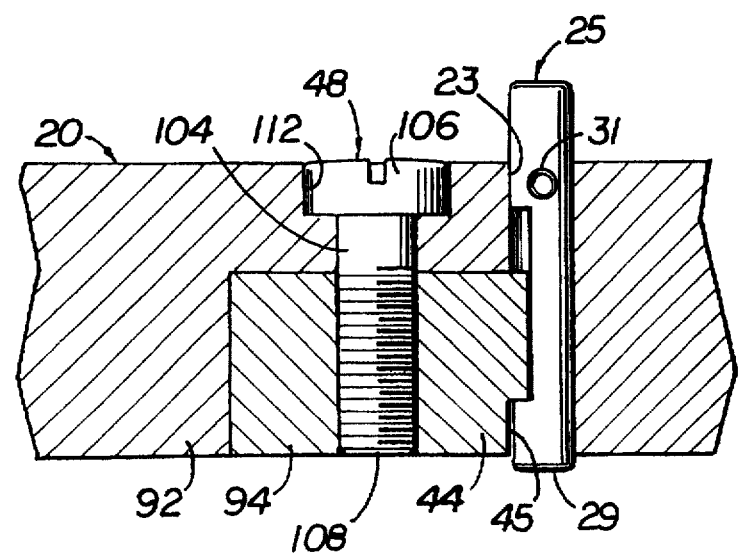
FIG. 7A is a detail cross-section view of the present invention taken along lines 7—7 of FIG. 5 showing the locking pin in the locked position.

As shown in FIGS. 1–7A, and especially in FIGS. 6–7A, the invention provides a closed lever position locking means of the first embodiment. A transverse notch 45 in the actuator arm 44 which is in alignment with a bore 23 through the base 20 when the lever 34 is in the closed position, and a locking pin 25 having a first portion 27 and a second portion 29 movable between an unlocked position and a locked position such that when the locking pin 25 is in the unlocked position (FIG. 7) the first portion 27 permits the actuator rod 56 to move distally or proximally, and when the locking pin 25 is in the locked position (FIG. 7A) in communication with the transverse notch 45 in the actuator arm 44, the second portion 29 prevents the actuator rod 56 from being displaced. As shown, the locking pin 25 is maintained in position within the bore 23 by an internal spring 31.

The invention can also have a flush port 18 in the bottom surface 24 of the base 20, which is in communication with the actuator rod 56, body member 80 and hollow elongated tube 88. This flush port 18 permits rinsing the internal compartments of the instrument to remove debris, such as coagulated blood and tissues. A bushing seal 19 directs the flow of rinsing solution distally past the actuator rod 56.

In a second embodiment, as seen particularly in FIGS. 8–11, the invention also contemplates that the distal end 232 of the base 220 may be adapted for selective rotation along an axis in alignment with the longitudinal axis of the base 220, thereby allowing the surgical tool 212 to selectively rotate. More specifically, a rotatable tool positioning collar 281 can be mounted on the body member 280 of the tool 212 adjacent the opening of the body portion 282 of the base 220. The collar 281 has a plurality of radial detents 283 thereon. A set screw 291 is positioned through a receptacle on the collar 281 to affix the collar 281 to the body member 280 of the tool 212, such that rotation of the collar 281 causes rotation of the body member 280 and the tool 212.

A set pin 285 of a size corresponding to the detents 283 is disposed adjacent the distal end 232 of the body portion 221 of the base 220 to be in selective communication with the detents 283 of the rotatable tool positioning collar 281. As shown in FIGS. 8 and 10, the set pin 285 is spring-loaded from the rear and is connected to a release tab 287 journalled through an elongated slot. The set pin 285 may be moved out of communication with the detents 283 to rotate the collar 281 by pulling the release tab 287 rearward against the spring-load. The set pin 285 has a bullet-shaped tip 275 corresponding to the tapered shape of the detents 283 such that more secure positioning of the collar 281 can be achieved.

Figure 12:
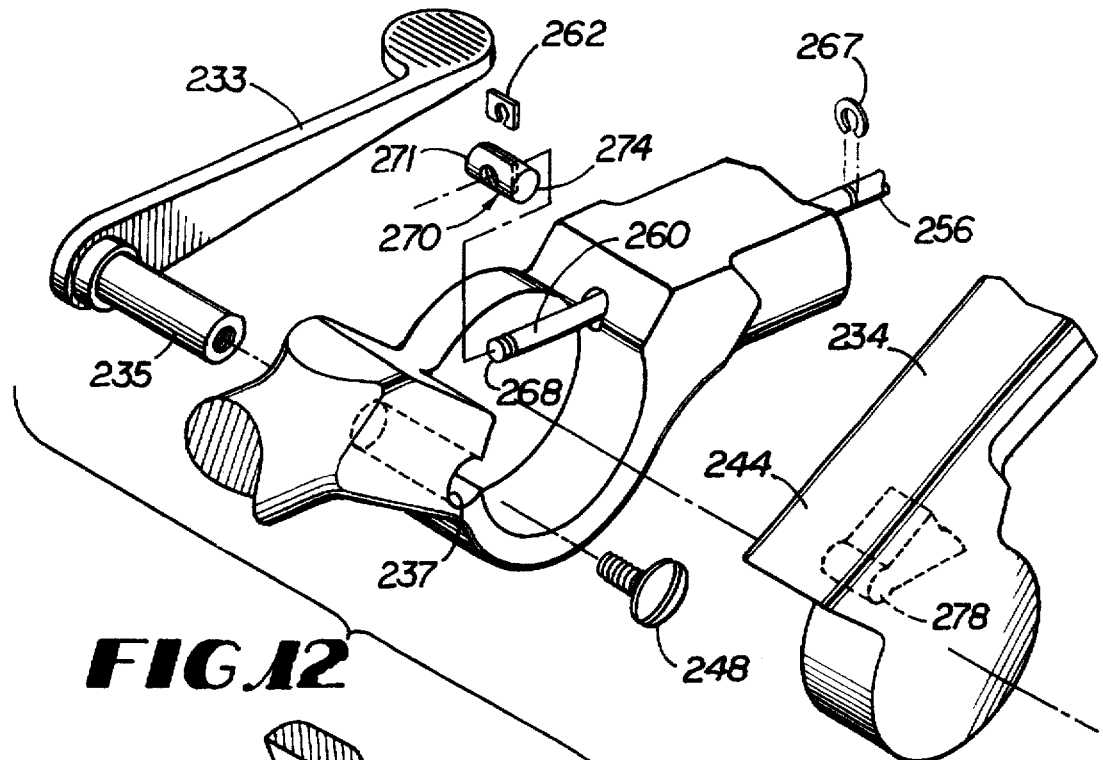
FIG. 12 is an exploded right-side perspective view of the selective lever position locking means of the second embodiment of the invention.

Referring to the second embodiment shown in FIG. 12, the actuator rod 256 may be pivotally connected to the actuator arm 244 wherein the first end 260 of the actuator rod 256 comprises a rearward end 268, and further comprising a barrel-shaped actuator cuff 270 having a first end 271 with a complimentarily internal opening for receiving the rearward end 268 of the actuator rod 256, which is maintained in place by the "C" clip 262. Additional "C" clip 267 can be provided to maintain the spring (not shown) in place around the actuator rod 256. The actuator rod 256 has a second end 274 comprising a pin 276 which is inserted into a complimentary receptacle 278 on the actuator arm 244. This second embodiment is preferred with the rotatable tool orienting means feature described above to prevent unthreading of the actuator rod 256.

As shown in FIGS. 8, 9 and 12, the second embodiment provides one means for securing the handle lever 234 at selected points throughout a range of motion defined between and including the open position and the closed position. The securing means can be a friction clutch 233 having a first portion 235 rotatably disposed through a bore 237 in the base 220 in selective communication with the actuator arm 244 and adapted for movement between a locked position and an unlocked position, such that when the clutch 233 is in the locked position, the first portion 235 increases friction against the actuator arm 244 preventing movement of the lever 234, and when the clutch 233 is in the unlocked position the first portion 235 decreases friction against the actuator arm 244, permitting movement of the lever 234. This embodiment also has a single means for connecting the clutch 233, the actuator arm 244 and the base 220 together, shown as a threaded fixation screw 248.

Figure 13:
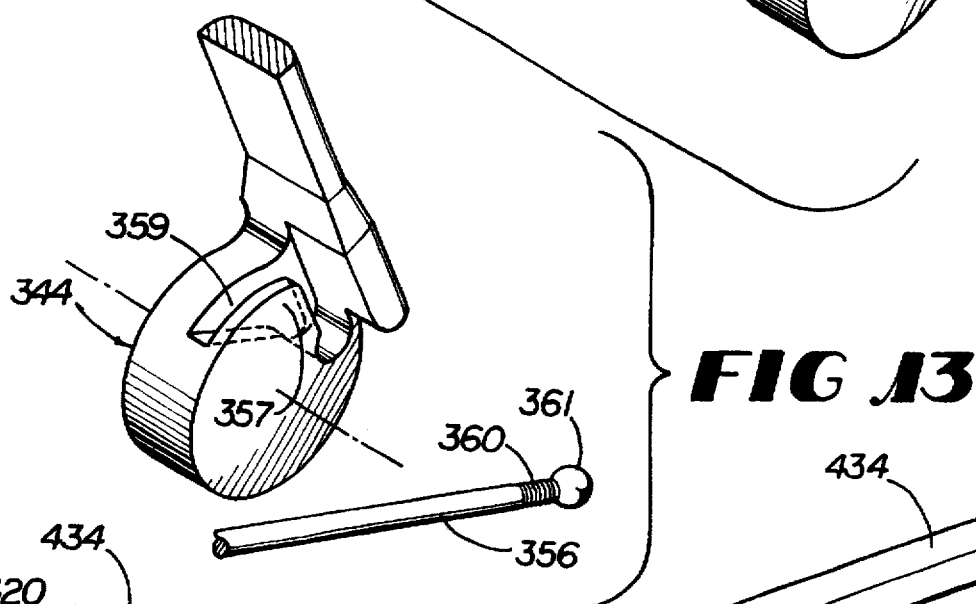
FIG. 13 is a detail left-side perspective view of an alternate actuator arm of a third embodiment of the present invention.

FIG. 13 shows an alternate actuating means of the third embodiment of the present invention. The actuator rod 356 has a rounded, or beaded, tip 361 on the first, or proximal, end 360 thereof. The beaded tip 361 is received within a corresponding slot 359 on the actuator arm 344. The end of the slot 359 corresponding to the beaded tip 361 is larger than the rest of the slot 359 due to a narrowing wall portion 357 on the actuator arm 344. Thus, when the lever 334 is in the normally open and operable position, the actuator rod 356 is prevented from displacement within the slot 359. The actuator rod 356 may be removed from the left-side only when the lever 334 is in the fully closed position. Moreover, in this embodiment the actuator rod 356 serves to maintain the actuator arm 344 in pivotal connection to the base (not shown) at the first predetermined point (not shown), without the need for additional fastening means. Therefore, this third embodiment also provides an alternative single connecting means.

Figures 14, 15:
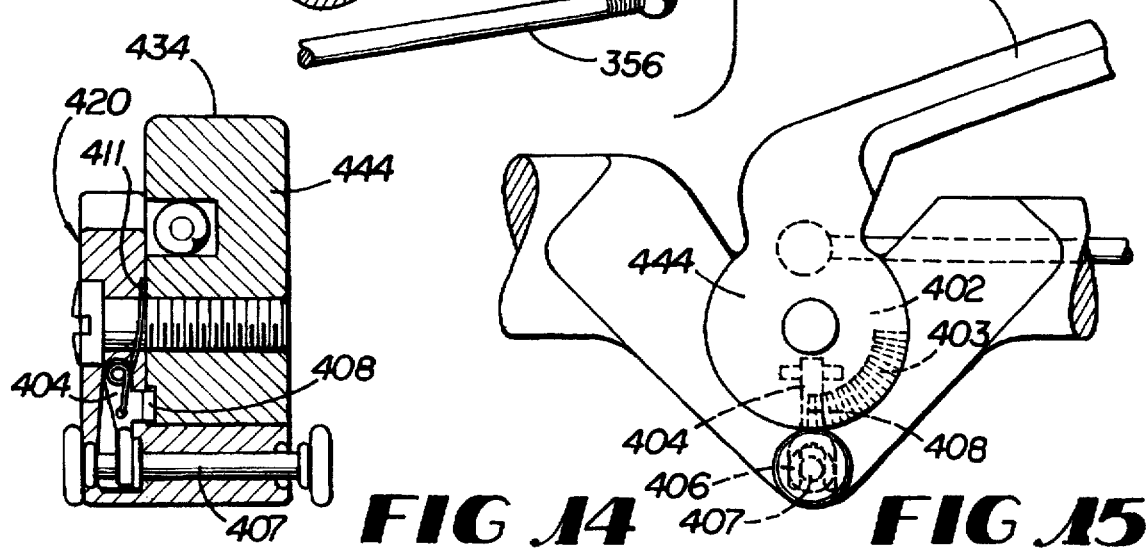
FIG. 14 is a front detail sectional view of a fourth embodiment of the present invention taken along the axis of actuator arm rotation showing the rachet and pawl of an alternative selective lever position locking means.
FIG. 15 is a right-side detail elevational view of the fourth embodiment showing the lever position locking means in phantom lines.

FIGS. 14 and 15 show the fourth embodiment having a means for securing the handle lever 434 at selected points throughout a range of motion. The securing means is shown as a rachet system having a rachet plate 402 having a toothed surface 403 thereon mounted on the actuator arm 444, and a pawl arm 404 having a pawl tooth 408 complementary to the rachet plate teeth 403. The pawl arm 404 has a notch 406 therein, and is pivotally mounted upon the base 420, such that the pawl tooth 408 is capable of selectively engaging the toothed surface 403 of the rachet plate 402 throughout the range of motion of the lever 434. A rachet lever 407 is disposed though the base 420 in communication with the notch 406 on the pawl arm 404, the rachet lever 407 being pivotally mounted within the base 420 such that the rachet lever 407 is moveable between a locked position, wherein the pawl tooth 408 is in engagement with the rachet plate 402, and an unlocked position, wherein the pawl tooth 408 is disengaged from the rachet plate 402. The pawl tooth 408 is releasably biased into engagement with the rachet plate 402 by a compression spring 411 disposed between the pawl arm 404 and the actuator arm 444.

FIGS. 16 and 17 show a fifth embodiment of the present invention having a means for securing the lever 534 at selected point throughout a range of motion. The securing means is shown as an alternative rachet system having a rachet plate 502 having a toothed surface 503 thereon mounted on the base 520, and a pawl arm 504 having a pawl tooth 508 complementary to the rachet plate teeth 503 which is pivotally mounted upon the lever 534 such that the pawl tooth 508 is capable of selectively engaging the toothed surface 503 of the rachet plate 502 throughout the range of motion of the lever. A pawl lever 507 is pivotally mounted on the lever 534 in communication with the pawl arm 504 such that the pawl lever 507 is moveable between a biased position (FIG. 17), wherein the pawl tooth 508 is in engagement with the rachet plate 502, and an unlocked position (FIG. 16), wherein the pawl tooth 508 is disengaged from the rachet plate 502. The pawl tooth 508 is releasably biased into engagement with the rachet plate 502 by a compression spring 511 disposed between the handle lever 534 and the pawl lever 507.

FIGS. 18 and 19 show a sixth embodiment of the present invention. The first, or proximal, end 660 of the actuator rod 656 is fitted with an adapter 663 with a beaded tip 661. The beaded tip 661 is rotatably received in a corresponding slot 659 on the actuator arm 644. The opposite, or distal, end 662 of the adapter 661 has internal threads corresponding to threads on the first end 660 of the actuator rod 656, however, a variety of constructions are possible. As shown, the adapter 663 has a larger diameter at the distal end 662 than the actuator rod 656, such that the first end 624 of the compression spring 652 lever biasing means is maintained adjacent the distal end 662 of the adapter 663 and in longitudinal alignment with the longitudinal axis, without the use of tensioning nuts used in the first embodiment. The second end 622 of the compression spring 652 is abutted adjacent the bushing seal 619. This embodiment also shows that the proximal end of the body member 680 of the tool 612 can be flared to abut against the hollow elongated tube 688. In addition to the set screw 689 against the hollow tube 688, the flared proximal end of the body member 680 of the tool 612 serves to maintain the tool 612 in position within the handle base 620 during normal use and rotation.

FIGS. 20–23 show a seventh embodiment of the present invention having a tool positioning means for rotating the tool 710 to a desired radial orientation with respect to the base 720 and adjustably securing the tool 710 at the desired radial orientation. As shown in the figures, the preferred tool positioning means comprises a rotatable tool orienting collar 750, at least one outwardly extending protrusion 760, and a collar biasing means.

The rotatable tool orienting collar 750 has a rear end 754 adjacent the distal end 722 of the base 720 and an opposite forward end 752. The rear end 754 of the collar 750 defines a plurality of radial detents 756 therein. The collar 750 is slidably mounted on the tool 710 so that the collar 750 slides longitudinally along the tool 710 between an extended position and a retracted position.

The tool positioning means also comprises at least one outwardly extending protrusion 760 adjacent the distal end 722 of the base 720. The protrusion 760 is of a size to be complementarily received within one detent 756 in the collar 750. This interrelationship is shown in FIG. 22. Alternatively, as shown in FIG. 23, the protrusions 760 are disposed on the distal end of the base to form a toothed surface 762 and the detents 756 in the collar 750 form a complementary "V" grooved surface 764. The protrusions 760 are in selective communication with the detents 756, thereby allowing the tool 710 to be disposed at the desired radial orientation.

The tool positioning means also comprises a collar biasing means for biasing the collar 750 towards the distal end 722 of the base 720. As shown in the FIGS. 20 and 21, the collar biasing means is a collar spring 765 having a first end 766 connected to the tool 710 and a second end 768 connected to the collar 750. The first end 766 of the collar spring 765 can be connected to the tool 710 by an outer sleeve attached to the outer surface of the tool 710 or any other retaining means. The collar 750 can have an opening therein adjacent its forward end 752 that complementarily receives the second end 768 of the collar spring 765. Thus, the collar spring 765 is secured between the collar 750 and the tool 710 so that it biases the collar 765 toward the base 720.

Preferably, the tool 710 has an axial slot 712 therein and a set screw 759 is disposed through the collar 750 to be in communication with the axial slot 712 in the tool 710. Thus, the set screw 759 allows the collar 750 to move longitudinally between the extended and retracted positions along predetermined path.

The collar 750 is in the extended position in FIG. 21, in which the collar 750 is moved longitudinally away from the base 720. The collar spring 765 is compressed and the set screw 759 is at the position furthest away from the distal end 722 of the base 720. Accordingly, the protrusion 760 is not disposed within the detent 756 and the collar 750 can then be rotated. Rotation of the collar 750 also rotates the tool 750 to be disposed at the desired radial orientation.

After rotating the tool to the desired radial orientation, the protrusion 760 is then disposed within a selected one of the detents 756 by the collar biasing means. That is, the collar 750 is released to the retracted position and maintained there by the collar biasing means, thereby adjustably securing the tool in the desired radial orientation. This is shown in FIG. 20, in which the collar 750 is adjacent the base 720 so that the collar spring 765 is extended and the set screw 759 is at the position in the axial slot 712 closest to the distal end 722 of the base 720.

The tool positioning means can further comprise a means for restricting longitudinal movement of the tool 710 relative to the base 720. In the embodiment shown in FIG. 20, the tool 710 has an annular slot 714 and the longitudinal movement restricting means comprises a dog point set screw 724 disposed through the body portion of the base 720 so that it is in communication with the annular slot 714. Thus, the dog point set screw 724 allows rotation of the tool 710 within the base 720 when the collar 750 is in the extended position, but prevents longitudinal movement of the tool 710.

11

The eighth embodiment of the present invention is shown in FIGS. 24-26. This embodiment comprises a means for securing the handle lever 834 at selected points throughout its range of motion and a means for selectively disengaging the securing means.

The securing means positions the handle lever 834 at selected points throughout its range of motion between and including the open position and the closed position. The securing means comprises a rachet plate 802 and a pawl arm 804. The rachet plate 802 has a toothed surface 803 thereon mounted on the base 820. The pawl arm 804 has a pawl tooth 808 complementary to the rachet plate teeth 803 and pivotally mounted upon the lever such that the pawl tooth 808 is capable of selectively engaging the toothed surface 803 of the rachet plate 802 throughout the range of motion of the lever 834.

The means for selectively disengaging the securing means comprises a pawl detachment member 811 having a first end 813 fixedly attached to the pawl arm 804 and an opposite second end 815. As shown in FIGS. 24-26, the second end 815 has a finger button 819 slidably mounted thereon. The pawl detachment arm 811 places the pawl arm 804 in the engaging or disengaging position relative to the rachet plate 802.

When in the disengaging position, which is shown in FIG. 24, the pawl arm 804 does not contact the toothed surface 803 of the rachet plate 802. The finger button 819 is disposed so that it is secured against the handle 834. When in this position, there is no contact between the pawl arm 804 and the rachet plate 802. Thus, the handle 834 can be freely moved between the open and closed position.

In the engaging position, which is shown in FIGS. 25 and 26, the finger button 819 is moved so that it is not secured to the handle 834, as in the disengaging position. In the engaging position, the pawl detachment member 811 is moveable between a locked position (FIG. 26), wherein the pawl tooth is in engagement with the rachet plate 802, and an unlocked position (FIG. 25), wherein the pawl tooth 808 is disengaged from the rachet plate 802.

The pawl tooth 808 is releasably biased into engagement with the rachet plate 802 by a compression spring 817 disposed between the handle lever 834 and the pawl arm 804. In the unlocked position, the finger button 819 must be downwardly disposed to overcome the force of the compression spring 817 and separate the pawl arm 804 from the rachet plate 802.

Since the handle 834 is biased to the open position, a downward force is applied to it to close it relative to the base 820. When in the engaging position, downward movement is maintained at a desired position by the interface of the pawl arm 804 with the rachet plate 802. The pawl arm 804 can then be released from the toothed surface 803 by moving it to the unlocked position, as shown in FIG. 25, or continue with further downward movement of the handle 834 in the locked position.

It is contemplated that the present invention may be utilized on any suitable surgical instrument with an articulated member on the tool including, but not limited to, conventional hand-held surgical instruments and minimally invasive surgical instruments, such as endoscopic and arthroscopic instruments. The instruments of the present invention may be constructed from any suitable material, such as metal or plastic. Examples of metals include stainless steel, aluminum and titanium. Examples of plastics include acetal, polycarbonate, ABS, and the like.

Although the present invention has been described with reference to specific details of certain embodiments thereof, it is not intended that such details should be regarded as limitations upon the scope of the invention except as and to the extent that they are included in the accompanying claims.

We claim:

1. A hand-held surgical instrument handle adapted to be attached to a tool having at least one articulated member thereon, the handle comprising:

a) an elongated base having a body portion, a top surface, an opposite bottom side, a first side, an opposite second side, a proximal end, and a distal end;

b) an elongated lever having a first surface, an opposite second surface, a front end, a rear end and an actuator arm adjacent the rear end adapted to be projected into the body portion of said base at a predetermined point;

c) means for connecting said actuator arm to said base at the predetermined point to allow said lever to pivot about a transverse axis at the predetermined point between a normally open position and a closed position;

d) means for actuating the articulated member of said tool when said lever is moved to the closed position;

e) means for biasing said lever in the normally open position;

f) means for securing said handle lever at selected points throughout a range of motion of said handle lever between and including the open position and the closed position, wherein said securing means is a rachet comprising:

i) a rachet plate having a toothed surface thereon mounted on said base; and ii) a pawl arm having a pawl tooth complementary to the rachet plate teeth pivotally mounted upon said lever such that said pawl tooth is capable of selectively engaging the toothed surface of said rachet plate throughout the range of motion of said lever; and g) means for selectively disengaging said securing means, comprising a pawl detachment member having a first end fixedly attached to said pawl arm and an opposite second end so that said pawl detachment member moves said pawl arm between an engaging position and a disengaging position, wherein said pawl tooth in the engaging position is movable between a locked position, wherein said pawl arm is in engagement with said rachet plate, and an unlocked position, wherein said pawl tooth is disengaged from said rachet plate, and wherein said pawl tooth in the disengaging position is disengaged from said rachet plate.

2. A hand-held surgical instrument handle adapted to be attached to a tool having at least one articulated member thereon, the handle comprising:

a) an elongated base having a body portion, a top surface, an opposite bottom side, a first side, an opposite second side, a proximal end, and a distal end;

b) an elongated lever having a first surface, an opposite second surface, a front end, a rear end and an actuator arm adjacent the rear end adapted to be projected into the body portion of said base at a predetermined point;

c) means for connecting said actuator arm to said base at the predetermined point to allow said lever to pivot about a transverse axis at the predetermined point between a normally open position and a closed position;

d) means for actuating the articulated member of said tool when said lever is moved to the closed position, wherein said actuating means comprises an actuator rod pivotally connected at a fixed point on the actuator arm of said lever such that moving said lever from the normally open position to the closed position causes said fixed point on the actuator arm to be displaced distally;

e) means for biasing said lever in the normally open position;

f) means for securing said handle lever at selected points throughout a range of motion of said handle lever between and including the open position and the closed position; and g) means for selectively disengaging said securing means.

3. The handle of claim 2, wherein said lever biasing means comprises a compression spring having a pre-selected thickness, a first end, a second end and a middle portion longitudinally circumscribing said actuator rod within said base, the first end being positioned adjacent said actuator rod and the second end being distally positioned adjacent the base, thereby biasing the actuator rod proximally and biasing said lever in the normally open position.

4. The handle of claim 2, wherein said actuator rod further comprises a first end and a second end, the second end of said rod being connectable to the articulated member of said tool and the first end of said rod being connected to said actuator arm at the fixed point, and wherein said rod is disposed through the body portion of said base such that movement of said lever from the normally open position to the closed position causes the first end of said rod to be displaced toward the distal end of said body portion of said base, thereby moving the articulated member of said tool.

5. A hand-held surgical instrument handle adapted to he attached to a tool having at least one articulated member thereon, the handle comprising:

a) an elongated base having a body portion, a top surface, an opposite bottom side, a first side, an opposite second side, a proximal end, and a distal end;

b) an elongated lever having a first surface, an opposite second surface, a front end, a rear end and an actuator arm adjacent the rear end adapted to be projected into the body portion of said base at a predetermined point;

c) means for connecting said actuator arm to said base at the predetermined point to allow said lever to pivot about a transverse axis at the predetermined point between a normally open position and a closed position;

d) means for actuating the articulated member of said tool when said lever is moved to the closed position;

e) means for biasing said lever in the normally open position;

f) means for securing said handle lever at selected points throughout a range of motion of said handle lever between and including the open position and the closed position;

g) means for selectively disengaging said securing means; and h) a joint comprising:
 i) a circular hinge socket on said base at the predetermined point which is journalled for motion about the transverse axis; and
 ii) a hinge barrel on said actuator arm dimensioned to be received within said hinge socket such that said actuator arm pivots about the transverse axis at the predetermined point when said lever is moved between the normally open position and the closed position.

6. The handle of claim 5, wherein said connecting means comprises a continuous bore extending along the transverse axis through said base at the predetermined point and through said actuator arm, said bore on said actuator arm having internal threads to receive a fixation screw having a head end and an opposite tail end having threads complimentary to said internal threads, said screw passing through said bore of said base such that the head end of said screw rests within a counterbore on the first side of said base.

\* \* \* \* \*